(12) United States Patent
Park

(10) Patent No.: US 9,694,031 B2
(45) Date of Patent: Jul. 4, 2017

(54) CALCIUM CARBONATE COMPOSITION FOR AMELIORATING, PREVENTING AND TREATING OSTEOPOROSIS, AND MANUFACTURING METHOD THEREFOR

(71) Applicants: MEDIENCE CO., LTD., Gangwon-do (KR); SMARTNUTRI CO., LTD., Gyeonggi-do (KR)

(72) Inventor: Sang Jae Park, Youngin-si (KR)

(73) Assignee: MEDIENCE CO., LTD., Chuncheon-si (KR)

( * ) Notice: Subject to any disclaimer, the term of this patent is extended or adjusted under 35 U.S.C. 154(b) by 0 days.

(21) Appl. No.: 15/318,315

(22) PCT Filed: Jun. 12, 2015

(86) PCT No.: PCT/KR2015/005960
§ 371 (c)(1),
(2) Date: Dec. 12, 2016

(87) PCT Pub. No.: WO2015/190882
PCT Pub. Date: Dec. 17, 2015

(65) Prior Publication Data
US 2017/0119815 A1    May 4, 2017

(30) Foreign Application Priority Data
Jun. 13, 2014 (KR) .................. 10-2014-0071795

(51) Int. Cl.
| A61K 33/10 | (2006.01) |
| C01F 11/18 | (2006.01) |
| A61K 9/00 | (2006.01) |
| A61K 9/68 | (2006.01) |
| A61K 9/16 | (2006.01) |
| A61K 9/20 | (2006.01) |
| A61K 9/48 | (2006.01) |
| A61K 47/02 | (2006.01) |
| A61K 47/36 | (2006.01) |
| A61K 47/14 | (2017.01) |
| A23L 33/16 | (2016.01) |

(52) U.S. Cl.
CPC .............. *A61K 33/10* (2013.01); *A23L 33/16* (2016.08); *A61K 9/0019* (2013.01); *A61K 9/0056* (2013.01); *A61K 9/0058* (2013.01); *A61K 9/0095* (2013.01); *A61K 9/16* (2013.01); *A61K 9/1611* (2013.01); *A61K 9/1617* (2013.01); *A61K 9/1652* (2013.01); *A61K 9/20* (2013.01); *A61K 9/205* (2013.01); *A61K 9/2009* (2013.01); *A61K 9/2013* (2013.01); *A61K 9/48* (2013.01); *A61K 9/485* (2013.01); *A61K 9/4858* (2013.01); *A61K 9/4866* (2013.01); *A61K 47/02* (2013.01); *A61K 47/14* (2013.01); *A61K 47/36* (2013.01); *A23V 2002/00* (2013.01)

(58) Field of Classification Search
None
See application file for complete search history.

(56) References Cited

U.S. PATENT DOCUMENTS 5,750,086 A * 5/1998 You .................. B82Y 30/00
423/431

FOREIGN PATENT DOCUMENTS

| CN | 101716194 A | 6/2010 |
| KR | 10-1996-0010009 A | 4/1996 |
| KR | 10-2008-0092738 A | 10/2008 |
| KR | 10-1152688 B1 | 6/2012 |
| KR | 10-2013-0068013 A | 6/2013 |

\* cited by examiner

*Primary Examiner* — Jeffrey T Palenik
(74) *Attorney, Agent, or Firm* — Maschoff Brennan

(57) ABSTRACT

The present invention relates to a calcium carbonate composition for ameliorating, preventing and treating osteoporosis, and a manufacturing method therefor. More specifically, the present invention relates to a calcium carbonate composition for alleviating, preventing and treating osteoporosis, the composition comprising calcium, magnesium and zinc, and having calcium carbonate microparticles formed by the supply of carbon dioxide gas. The present invention provides a composition for maximizing the absorption of calcium, the composition being developed as a health food, food material or the like, and displaying the effects of relieving and alleviating illnesses and symptoms caused by a lack of calcium.

8 Claims, No Drawings

CALCIUM CARBONATE COMPOSITION FOR AMELIORATING, PREVENTING AND TREATING OSTEOPOROSIS, AND MANUFACTURING METHOD THEREFOR

TECHNICAL FIELD

The present invention relates to a calcium carbonate composition for alleviating, preventing, and treating osteoporosis, and a manufacturing method therefor.

BACKGROUND ART

Calcium is one of the most important inorganic substances for a human body, and the absorption of calcium into the human body differs according to a taking method, a composition, and a dosage form of calcium.

Since calcium is used to build most of the bones and teeth, low calcium absorption inevitably results in osteoporosis. Osteoporosis is a degenerative disease which is caused by a continuous loss of calcium in bones, and adults aged 35 to 40 years are commonly affected with osteoporosis and osteoporosis is more common in women than men.

In the case of growing children, a lack of calcium may give rise to negative results such as hampering the growth of height and leading deformity. Therefore, it is important to get enough calcium into the body.

To achieve this, modern people take calcium agents as health supplement food. Calcium agents include calcium carbonate, calcium sulfate, calcium phosphate, calcium oxide, calcium hydroxide, calcium nitrate, calcium lactate, calcium citrate, calcium gluconate, or the like. From among these, calcium gluconate can be fast absorbed into the body, but its price is expensive and thus calcium gluconate is not frequently used. Calcium carbonate is cheap and thus is most frequently used from among calcium agents. However, in the case of calcium carbonate, an absorption rate is noticeably low and there is a problem that a substantial absorption rate is very low in comparison to an intake.

In addition, animal materials such as eggshells, cow bones, or the like which are used as natural calcium are avoided due to infectious diseases of animals. In addition, there was a report that a disease was communicated from animals to humans due to the use of animal materials, and some people have an aversion to animal materials. Therefore, there is a need for a calcium material which is cheap and a product which can promote the absorption of calcium.

Accordingly, the inventors of the present invention have found that calcium carbonate manufactured in the form of "a divalent metal ion compound" and "a size of a nano level", rather than in a related-art method of manufacturing calcium in the form of a single component and then mixing, showed a higher body absorption effect than in the case of a normal intake of calcium, and had the effect of preventing and treating osteoporosis, and completed the present invention.

DETAILED DESCRIPTION OF THE PRESENT DISCLOSURE

Technical Objects

The present invention provides a calcium carbonate composition which can promote absorption of calcium into a human body, and can effectively alleviate, prevent, and treat osteoporosis, and a manufacturing method therefor.

Technical Solving Means

In order to achieve the above-mentioned object, the present invention provides a method for manufacturing a calcium carbonate composition. The method may include the steps of: (A) producing a mixture by dispersing calcium, magnesium, and zinc in water; (B) supplying a carbon dioxide gas to the mixture after step (A); and (C) drying after step (B). In step (A), the mixture may be produced by dispersing 0.015-0.8 parts by weight of magnesium and 0.015-0.45 parts by weight of zinc per every 100 parts by weight of calcium in water.

In the method for manufacturing the calcium carbonate composition of the present invention, calcium carbonate microparticles may be formed by carbonatizing calcium by supplying the carbon dioxide gas. In the process of supplying the carbon dioxide gas, excessively large particles can be prevented from being formed and fusion between particles can be prevented, such that a nano condition can be maintained. In addition, by adding very small amounts of zinc and magnesium to calcium, the absorption of calcium into the body can be enhanced. When parts by weight of magnesium and zinc per every 100 parts by weight of calcium are less than 0.015, the effect of promoting the absorption of calcium may be reduced, and, when parts by weight of magnesium per every 100 parts by weight of calcium is greater than 0.8 and parts by weight of zinc is greater than 0.45, an additional enhancement effect in comparison to an amount of input is not expected and this condition may not be economical.

The method for manufacturing the calcium carbonate composition may further include, after step (B), adding a dispersant and additionally supplying a carbon dioxide gas, and may further include, after additionally supplying the carbon dioxide gas, adding an emulsifier. The dispersant is added to manufacture calcium particles of a size less than micrometer. The addition of the dispersant can prevent the calcium carbonate particles from growing and can maintain the calcium carbonate particles of a nano size. In addition, the emulsifier can enhance the dispersive power of the calcium carbonate particles In the method for manufacturing the calcium carbonate composition of the present invention, the calcium may be derived from one or more selected from calcium hydroxide and calcium oxide.

In the method for manufacturing the calcium carbonate composition of the present invention, the magnesium may be derived from one or more selected from magnesium hydroxide, magnesium oxide, magnesium chloride, magnesium stearate, magnesium phosphate, magnesium silicate, magnesium lactate, magnesium gluconate, magnesium sulfate, and magnesium phytate.

In the method for manufacturing the calcium carbonate composition of the present invention, the zinc may be derived from one or more selected from zinc oxide, zinc sulfate, and zinc gluconate.

In the method for manufacturing the calcium carbonate composition of the present invention, the dispersant may be a dispersant commonly used in the relevant prior art, and preferably, the dispersant may be one or more selected from xanthane gum, carboxymethylcellulose, poly gamma glutamic acid, alginic acid, guar gum, dextrin, starch, Arabia gum, lecithin, whey protein, and soybean protein, and 1-40 parts by weight of the dispersant per every 100 parts by weight of calcium may be added. When the above-mentioned range is satisfied, the growth of the calcium carbonate particles can be inhibited, controlled, and maintained. When the concentration of the added dispersant is high, viscosity may increase and liquidity may be reduced, and also, the growth of the calcium carbonate particles may be excessively inhibited. When the concentration of the dispersant is low, the effect of adjusting the growth of the calcium carbonate particles may not be obtained.

In the method for manufacturing the calcium carbonate composition of the present invention, the emulsifier may be an emulsifier commonly used in the relevant prior art, and preferably, the emulsifier may be one or more selected from fatty acid ester and sorbitan stearate, and 1% (v/v) or less of the emulsifier may be added in comparison to the volume of the mixture before being dried. When more than 1% (v/v) of the emulsifier is added, an emulsifying effect does not increase in comparison to an amount of input and this condition may not be economical.

In addition, the present invention provides a calcium carbonate composition containing 0.015-0.8 parts by weight of magnesium and 0.015-0.45 parts by weight of zinc per every 100 parts by weight of calcium.

In addition, the present invention provides a food composition for alleviating osteoporosis, containing the calcium carbonate composition described above.

The food composition for alleviating osteoporosis according to the present invention may contain 0.00001-90 wt % of the calcium carbonate composition in comparison to the food composition. When the calcium carbonate composition content is less than 0.00001 wt %, a marginal effect may be obtained, and, when the calcium carbonate composition content exceeds 90 wt %, the effect is poor in comparison to usage and thus this condition may not be economical.

For example, the food composition for alleviating osteoporosis according to the present invention may be one or more selected from meat, grains, caffeine drinks, normal drinks, chocolate, bread, snack, confectionaries, candies, pizza, jelly, noodles, gums, dairy products, ice cream, alcoholic drinks, vitamin complexes, and other health supplement food, but is not limited to these.

In addition, the present invention provides a pharmaceutical composition for preventing and treating osteoporosis, containing the calcium carbonate composition described above.

The pharmaceutical composition for preventing and treating osteoporosis according to the present invention may contain 0.00001-90 wt % of the calcium carbonate composition in comparison to the pharmaceutical composition. When the calcium carbonate composition content is less than 0.00001 wt %, a marginal effect may be obtained, and, when the calcium carbonate composition content exceeds 90 wt %, the effect is poor in comparison to usage and thus this condition may not be economical.

The pharmaceutical composition for preventing and treating osteoporosis according to the present invention may further include a carrier, a diluent, or an excipient which is pharmaceutically allowable, in addition to active ingredients. The usable carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, hydroxymethyl benzoate, hydroxypropyl benzoate, talc, magnesium stearate, and mineral oil, and may use one or more selected therefrom. In addition, when the pharmaceutical composition for preventing and treating osteoporosis is a medicine, the pharmaceutical composition may further include one or more selected from a filler, an anti-agglomerating agent, a lubricant, a wetting agent, flavor, an emulsifier, or a preservative.

Formulation of the pharmaceutical composition for preventing and treating osteoporosis according to the present invention may be a preferable form according to a using method, and in particular, it is preferable to formulate the pharmaceutical composition for preventing and treating osteoporosis by adopting a well-known method, such that rapid, continuous, or delayed discharge of an active component can be provided after the composition is administered to a mammal. Examples of the formulation may be one selected from plasters, granules, locations, liniments, lemonades, aromatic waters, powders, syrups, liquids and solutions, aerosols, extracts, elixirs, ointments, fluidextracts, emulsions, suspensions, decoctions, infusions, tablets, suppositories, injections, sprits, cataplsma, capsules, creams, troches, tinctures, pastes, pills, and soft or hard gelatin capsules.

A dosage of the pharmaceutical composition for preventing and treating osteoporosis according to the present invention may be determined in consideration of an administration method and age, sex, weight, and severity of a disease of a taker. For example, 0.00001 to 100 mg/kg (weight) of the pharmaceutical composition for preventing and treating osteoporosis according to the present may be administered one or more times per day with reference to active ingredients. However, the above-mentioned dosage is merely an example and may be changed according to a taker's condition and doctor's prescription.

Advantageous Effect

The present invention provides a calcium carbonate composition for maximizing the absorption of calcium, and a manufacturing method therefor. When the composition is used as food and pharmaceutical materials, the effects of relieving and alleviating illnesses and symptoms caused by a lack of calcium can be obtained.

BEST MODE FOR EMBODYING THE INVENTION

Hereinafter, the present invention will be described in detail in the following examples, but the right scope of the present invention is not limited to the following examples, and includes a variation of the equivalent technical idea.

Example 1: Manufacturing Calcium Agent Composition 100 g of calcium hydroxide was dispersed in 1.5 L of water, and 0.193 g of magnesium hydroxide and 0.019 g of zinc oxide were added in sequence and then were dispersed in water. In this case, calcium, magnesium, and zinc have a weight ratio of 100:0.148:0.028. Carbon dioxide was bubbled and supplied for 30 minutes. Then, when pH of the solution reached 8.0, xanthan gum was added at a ratio of 0.5% (w/v) in comparison to the total volume of the solution (13.9 parts by weight of a dispersant per every 100 parts by weight of calcium) and was dissolved, and then, carbon dioxide was additionally bubbled and pH of the solution was made to reach 7.0. Thereafter, 139.2 g of a calcium agent composition of the present invention was acquired by adding 0.1% (v/v) of glycerin esters of fatty acids as an emulsifier, shaking and agitating, and then spraying and drying.

Comparison Examples 1 to 9: Manufacturing Calcium Agent Composition

Comparison Example 1

129 g of a calcium agent composition (comparison example 1) was acquired by dispersing 100 g of calcium hydroxide in 1.5 L of water, making pH of a solution reach 7.0 by bubbling carbon dioxide and supplying for 30 minutes, and then spraying and drying.

Comparison Example 2

129 g of a calcium agent composition (comparison example 2) was acquired by dispersing 100 g of calcium hydroxide and 0.193 g of magnesium hydroxide in 1.5 L of water, making pH of a solution reach 7.0 by bubbling carbon dioxide and supplying for 30 minutes, and then spraying and drying.

Comparison Example 3

129 g of a calcium agent composition (comparison example 3) was acquired by dispersing 100 g of calcium hydroxide and 0.019 g of zinc oxide in 1.5 L of water, making pH of a solution reach 7.0 by bubbling carbon dioxide and supplying for 30 minutes, and then spraying and drying.

Comparison Example 4

129 g of a calcium agent composition (comparison example 4) was acquired by dispersing 100 g of calcium hydroxide, 0.193 g of magnesium hydroxide, 0.19 g of zinc oxide in 1.5 L of water, making pH of a solution reach 7.0 by bubbling carbon dioxide and supplying for 30 minutes, and then spraying and drying.

Comparison Example 5

129 g of a calcium agent composition (comparison example 5) was acquired by dispersing 100 g of calcium hydroxide, 0.4 g of magnesium hydroxide, 0.019 g of zinc oxide in 1.5 L of water, making pH of a solution reach 7.0 by bubbling carbon dioxide and supplying for 30 minutes, and then spraying and drying.

Comparison Example 6

129 g of a calcium agent composition (comparison example 6) was acquired by dispersing 100 g of calcium hydroxide, 0.193 g of magnesium hydroxide, 0.45 g of zinc oxide in 1.5 L of water, making pH of a solution reach 7.0 by bubbling carbon dioxide and supplying for 30 minutes, and then spraying and drying.

Comparison Example 7

129 g of a calcium agent composition (comparison example 7) was acquired by dispersing 100 g of calcium hydroxide, 1.2 g of magnesium hydroxide, 0.019 g of zinc oxide in 1.5 L of water, making pH of a solution reach 7.0 by bubbling carbon dioxide and supplying for 30 minutes, and then spraying and drying.

Experimental Example 1: Estimating Enhanced Effect of Calcium Agent Composition on Osteoporosis In the present experimental example, an enhanced effect of the calcium agent composition acquired in example 1 on osteoporosis was estimated.

40 SD rats aged 7 weeks old, which were affected with osteoporosis by removing ovaries, were made to undergo an adaptation step by supplying feed for a week. Then, the SD rats were divided into four groups, an untreated group, a comparison example 1 administration group, an eggshell calcium administration group, and an example 1 administration group. Then, 20 mg of a calcium agent composition was diluted with distilled water and 1 ml was supplied every day for 16 weeks. After stopping supplying feed for 24 hours in the last week of the experiment, ratios of calcium and phosphorus of femur, a bone strength, and a maximum load were compared, and the result of the comparison was as in table 1 presented below:

TABLE 1

| | Ca/Ash (%) | P/Ash (%) | Bone Strength (N/mm) | Maximum Load (N) |
|---|---|---|---|---|
| Untreated Group | 24.2(±2.3) | 12.7(±1.5) | 116.1(±17.1) | 84.2(±7.3) |
| Comparison Example 1 | 26.9(±2.8) | 14.1(±2.0) | 121.5(±12.3) | 86.3(±8.5) |
| Example 1 | 30.1(±4.0) | 15.3(±1.9) | 148.3(±11.1) | 102.5(±4.1) |
| Eggshell Calcium | 25.1(±1.9) | 13.2(±1.9) | 118.3(±13.4) | 84.2(±6.9) |

As a result of the experiment, the material in example 1, which was the calcium agent composition of the present invention, showed the noticeably increased bone strength in the rats which were affected with osteoporosis. In addition, the calcium and phosphorus contents of the femur increased (table 1).

Experimental Example 2: Comparing and Estimating Enhanced Effect of Calcium Agent Composition on Osteoporosis In the present experimental example, the calcium agent composition acquired in examples 1 to 6 and the calcium agent compositions acquired in comparison examples 2 and 3 were compared and their advanced effects on osteoporosis were estimated.

8 SD rats aged 7 weeks old, which were affected with osteoporosis by removing ovaries, were divided into an untreated group, a comparison example 1 administration group, an eggshell calcium administration group, and an example 1 administration group. Then, 20 mg of a calcium agent composition was diluted with distilled water and 1 ml was supplied every day for 16 weeks. After stopping supplying feed for 24 hours in the last week of the experiment, ratios of calcium and phosphorus of femur were compared, and the result of the comparison was as in table 2 presented below:

TABLE 2

| Classification | Ca/Ash (%) | P/Ash (%) |
|---|---|---|
| Untreated Group | 25.1 | 12.8 |
| Example 1 | 31.0 | 15.2 |
| Comparison Example 2 | 27.9 | 14.8 |
| Comparison Example 3 | 28.1 | 13.9 |
| Comparison Example 4 | 30.8 | 15.1 |
| Comparison Example 5 | 30.7 | 14.9 |
| Comparison Example 6 | 30.9 | 15.0 |
| Comparison Example 7 | 30.6 | 14.9 |

As a result of the experiment, it was identified that the calcium and phosphorus content of the femur in example 1 was higher than in comparison examples 2 and 3 in which calcium includes only magnesium or zinc.

In addition, in example 1 of the present invention, calcium includes both magnesium and zinc, but it was identified that the calcium and phosphorus content of the femur in example 1 was higher than in comparison examples 4 to 7 in which a dispersant and an emulsifier were not used (table 2).

Example 2: Manufacturing Food Composition for Alleviating Osteoporosis

In this example, a food composition for alleviating osteoporosis was manufactured as follows.
(1) Manufacturing Mixed Grain Powder Powder of a particle size of 60 mesh was prepared in a grinder by pregelatinizing, drying, and roasting brown rice, barley, glutinous rice, and Job's tears in well-known methods. Powder of a particle size of 60 mesh was prepared by steaming, drying, roasting, and then grinding black beans, black sesame, and perilla. Thereafter, mixed grain powder was manufactured by mixing 30 wt % of brown rice, 15 wt % of Job's tears, 20 wt % of barley, 9 wt % of glutinous rice, 7 wt % of perilla, 8 wt % of black beans, 7 wt % of black sesame, 3 wt % of the calcium carbonate composition of the present disclosure, 0.5 wt % of ganoderma lucidum, and 0.5 wt % of foxglove.
(2) Manufacturing Chewing Gum A chewing gum was manufactured in a normal method by mixing 20 wt % of a gum base, 76.9 wt % of sugar, 1 wt % of a flavor, 2 wt % of water, and 0.1 wt % of the calcium carbonate composition of the present invention.
(3) Manufacturing Candy A candy was manufactured in a normal method by mixing 60 wt % of sugar, 39.8 wt % of starch syrup, 0.1 wt % of a flavor, and 0.1 wt % of the calcium carbonate composition of the present invention.
(4) Manufacturing Biscuit A biscuit was manufactured in a normal method by mixing 25.59 wt % of soft flour class 1, 22.22 wt % of medium flour class 1, 4.80 wt % of refined sugar, 0.73 wt % of table salt, 0.78 wt % of glucose, 11.78 of palm shortening, 1.54 wt % of ammonium, 0.17 wt % of sodium bicarbonate, 0.16 wt % of sodium bisulfate, 1.45 wt % of rice flour, 0.0001 wt % of vitamin B, 0.04 wt % of a milk flavor, 20.6998 wt % of water, 1.16 wt % of whole milk powder, 0.29 wt % of imitation milk powder, 0.03 wt % of mono calcium phosphate, 0.29 wt % of scattered salt, and 7.27 wt % of sprayed oil, and 1 wt % of the calcium carbonate of the present invention.
(5) Manufacturing Healthy Drink A healthy drink was manufactured in a normal method by mixing 0.26 wt % of honey, 0.0002 wt % of thioctic acid amide, 0.0004 wt % of nicotinic acid amide, 0.0001 wt % of riboflavin sodium hydrochloride, 0.0001 wt % of pyridoxine hydrochloride, 0.001 wt % of inositol, 0.002 wt % of orotic acid, 98.7362 wt % of water, and 1 wt % of the calcium carbonate composition of the present invention.
(6) Manufacturing Sausage A sausage was manufactured in a normal method by mixing 65.18 wt % of pork, 25 wt % of chicken, 3.5 wt % of starch, 1.7 wt % of a soybean protein, 1.62 wt % of table salt, 0.5 wt % of glucose, and 1.5 wt % of glycerine, and 1 wt % of the calcium carbonate composition of the present invention.
(7) Manufacturing Health Supplement Food Tablet type health supplement food was manufactured in a normal method by 55 wt % of spirulina, 10 wt % of guar gum enzyme hydrolysate, 0.01 wt % of vitamin B hydrochloride, 0.01 wt % of vitamin B6, 0.23 wt % of DL-methionine, 0.7 wt % of magnesium stearate, 22.2 wt % of lactose, and 1.85 wt % of corn starch, and 10 wt % of calcium carbonate composition of the present invention.

Example 3: Manufacturing Pharmaceutical Composition for Preventing and Treating Osteoporosis In the present example, a pharmaceutical composition for preventing and treating osteoporosis was manufactured as follows.
(1) Manufacturing Powders Powders were manufactured by mixing 1 g of the calcium carbonate composition of the present invention and 2 g of lactose and filling an air-tight bag with the mixture.
(2) Manufacturing Tablets Tablets were manufactured by mixing 100 mg of the calcium carbonate composition of the present invention, 100 mg of corn starch, 100 mg of lactose, and 2 mg of magnesium stearate and then tableting in a normal tablet manufacturing method.
(3) Manufacturing Capsules Capsules were manufactured by mixing 100 mg of the calcium carbonate composition of the present invention, 100 mg of corn starch, 100 mg of lactose, and 2 mg of magnesium stearate and then filling gelatin capsules with the mixture.
(4) Manufacturing Injections Injections were manufactured by dissolving 100 mg of the calcium carbonate composition of the present invention by applying an appropriate amount of distilled water for injection, adjusting pH to about 7.5, filling an ampule of 2 ml, and then sterilizing.

INDUSTRIAL APPLICABILITY

The present invention relates to a calcium carbonate composition for supplying calcium, which includes calcium, magnesium, and zinc. When calcium is provided in the form of the composition of the present invention, an absorption rate of calcium can be greatly enhanced, bones can be strengthened and osteoporosis can be prevented and treated. Therefore, the composition of the present invention may be developed as functional food materials and medicine materials and may help the growth of companies.

What is claimed is:

1. A method for manufacturing a calcium carbonate composition, the method comprising the steps of:
   (A) producing a mixture by dispersing calcium, magnesium, and zinc in water;
   (B) supplying a carbon dioxide gas to the mixture after step (A); and
   (C) drying after step (B),
   wherein, in step (A), the mixture is produced by dispersing 0.015-0.8 parts by weight of magnesium and 0.015-0.45 parts by weight of zinc per every 100 parts by weight of calcium in water.

2. The method of claim 1, further comprising, after step (B), adding a dispersant and additionally supplying a carbon dioxide gas.

3. The method of claim 2, further comprising, after additionally supplying the carbon dioxide gas, adding an emulsifier.

4. The method of claim 1, wherein the calcium is derived from one or more selected from calcium hydroxide and calcium oxide.

5. The method of claim 1, wherein the magnesium is derived from one or more selected from magnesium hydroxide, magnesium oxide, magnesium chloride, magnesium stearate, magnesium phosphate, magnesium silicate, magnesium lactate, magnesium gluconate, magnesium sulfate, and magnesium phytate.

6. The method of claim 1, wherein the zinc is derived from one or more selected from zinc oxide, zinc sulfate, and zinc gluconate.

7. The method of claim 2, wherein the dispersant is one or more selected from xanthane gum, carboxymethylcellulose, poly gamma glutamic acid, alginic acid, guar gum, dextrin, starch, Arabia gum, lecithin, whey protein, and soybean protein, and 1-40 parts by weight of the dispersant per every 100 parts by weight of calcium are added.

8. The method of claim 3, wherein the emulsifier is one or more selected from fatty acid ester and sorbitan stearate, and 1% (v/v) or less of the emulsifier is added to the mixture.

\* \* \* \* \*

UNITED STATES PATENT AND TRADEMARK OFFICE
CERTIFICATE OF CORRECTION

PATENT NO. : 9,694,031 B2  
APPLICATION NO. : 15/318315  
DATED : July 4, 2017  
INVENTOR(S) : Sang Jae Park Page 1 of 1

It is certified that error appears in the above-identified patent and that said Letters Patent is hereby corrected as shown below:

On the Title Page

In Column 1, Item (71), delete, "SMARTNUTRI CO., LTD., Gyeonggi-do (KR)".

Signed and Sealed this  
Fifth Day of September, 2017

Joseph Matal  
*Performing the Functions and Duties of the*  
*Under Secretary of Commerce for Intellectual Property and*  
*Director of the United States Patent and Trademark Office*